(12) United States Patent
Pan et al.

(10) Patent No.: US 11,084,026 B2
(45) Date of Patent: *Aug. 10, 2021

(54) CATALYST AND METHOD FOR PREPARING LIGHT OLEFINS BY DIRECT CONVERSION OF SYNGAS

(71) Applicant: DALIAN INSTITUTE OF CHEMICAL PHYSICS, CHINESE ACADEMY OF SCIENCES, Liaoning (CN)

(72) Inventors: Xiulian Pan, Liaoning (CN); Feng Jiao, Liaoning (CN); Xinhe Bao, Liaoning (CN)

(73) Assignee: DALIAN INSTITUTE OF CHEMICAL PHYSICS, CHINESE ACADEMY OF SCIENCES, Liaoning (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/618,751

(22) PCT Filed: Aug. 2, 2018

(86) PCT No.: PCT/CN2018/098379
§ 371 (c)(1),
(2) Date: Feb. 25, 2020

(87) PCT Pub. No.: WO2018/219365
PCT Pub. Date: Dec. 6, 2018

(65) Prior Publication Data
US 2021/0002184 A1  Jan. 7, 2021

(30) Foreign Application Priority Data

Jun. 2, 2017 (CN) .......................... 201710408018.9

(51) Int. Cl.
*B01J 35/00* (2006.01)
*B01J 23/06* (2006.01)
*B01J 29/70* (2006.01)
*B01J 37/04* (2006.01)
*B01J 21/04* (2006.01)
(Continued)

(52) U.S. Cl.
CPC ........... *B01J 35/0006* (2013.01); *B01J 21/04* (2013.01); *B01J 21/066* (2013.01); *B01J 21/08* (2013.01); *B01J 23/005* (2013.01); *B01J 23/06* (2013.01); *B01J 23/10* (2013.01); *B01J 23/26* (2013.01); *B01J 23/34* (2013.01); *B01J 29/7015* (2013.01); *B01J 29/85* (2013.01); *B01J 37/04* (2013.01); *C07C 1/043* (2013.01); *C07C 2521/04* (2013.01); *C07C 2521/06* (2013.01); *C07C 2521/08* (2013.01); *C07C 2523/06* (2013.01); *C07C 2523/10* (2013.01); *C07C 2523/26* (2013.01); *C07C 2523/34* (2013.01); *C07C 2529/70* (2013.01); *C07C 2529/85* (2013.01)

(58) Field of Classification Search
CPC ........ B01J 29/70; B01J 29/78; B01J 29/7015; B01J 29/7049; B01J 29/7065; B01J 29/783; B01J 29/82; B01J 29/83; B01J 29/84; B01J 29/85; B01J 29/87; B01J 29/89; B01J 2229/186; B01J 2229/18; B01J 35/0006; B01J 37/0036; B01J 37/04; B01J 37/28; B01J 37/30; B01J 23/005; B01J 23/06; B01J 23/16; B01J 23/26; B01J 23/34; B01J 23/64; B01J 23/54; B01J 23/6522; C07C 1/043; C07C 1/0435; C07C 1/0425; C07C 1/044; C07C 1/0445; C07C 1/0455; C07C 1/04; C07C 1/10; C07C 11/04; C07C 11/08; C07C 11/09; C07C 11/06
See application file for complete search history.

(56) References Cited

U.S. PATENT DOCUMENTS

2011/0201860 A1* 8/2011 Akhtar ...................... C07C 2/76
585/419

FOREIGN PATENT DOCUMENTS

CN 1083415 A 3/1994
CN 1537674 A 10/2004
(Continued)

OTHER PUBLICATIONS

Zhong et al., "Cobalt carbide nanoprisms for direct production of lower olefins from syngas", Nature 538, 84-87 (2016) doi:10.1038/nature19786.
(Continued)

*Primary Examiner* — Jafar F Parsa
(74) *Attorney, Agent, or Firm* — Novick, Kim & Lee, PLLC; Allen Xue

(57) ABSTRACT

A process for direct synthesis of light olefins uses syngas as the feed raw material. This catalytic conversion process is conducted in a fixed bed or a moving bed using a composite catalyst containing components A and B (A+B). The active ingredient of catalyst A is metal oxide; and catalyst B is an oxide supported zeolite. A carrier is one or more of $Al_2O_3$, $SiO_2$, $TiO_2$, $ZrO_2$, $CeO_2$, MgO and $Ga_2O_3$ having hierarchical pores; the zeolite is one or more of CHA and AEI structures. The loading of the zeolite is 4%-45% wt. A weight ratio of the active ingredients in the catalyst A and the catalyst B is within a range of 0.1-20, and preferably 0.3-5. The total selectivity of the light olefins comprising ethylene, propylene and butylene can reach 50-90%, while the selectivity of a methane byproduct is less than 15%.

14 Claims, No Drawings

(51) Int. Cl.
*B01J 21/06* (2006.01)
*B01J 21/08* (2006.01)
*B01J 23/00* (2006.01)
*B01J 23/10* (2006.01)
*B01J 23/26* (2006.01)
*B01J 23/34* (2006.01)
*B01J 29/85* (2006.01)
*C07C 1/04* (2006.01)

(56) References Cited

FOREIGN PATENT DOCUMENTS

| | | |
|---|---|---|
| CN | 106311317 A | 1/2017 |
| CN | 106345514 A | 1/2017 |
| JP | 2017087204 A | 5/2017 |
| WO | 2015084575 A2 | 6/2015 |

OTHER PUBLICATIONS

Jiao et al., "Selective conversion of syngas to light olefins", Science, vol. 351, Issue 6277, Mar. 4, 2016, pp. 1065-1068.

* cited by examiner

CATALYST AND METHOD FOR PREPARING LIGHT OLEFINS BY DIRECT CONVERSION OF SYNGAS

TECHNICAL FIELD

The present invention belongs to synthesis of light olefins using syngas, and particularly relates to a catalyst and a method for synthesizing light olefins via direct conversion of syngas.

BACKGROUND

Light olefins refer to alkenes with the number of carbon atoms less than or equal to 4. Light olefins, including ethylene, propylene and butene, are very important basic organic chemical raw materials. With the fast growth of economy in China, the market of the light olefins is in short supply for a long time. At present, the light olefins are produced mainly through a petrochemical route of cracking of light hydrocarbon (ethane, naphtha and light diesel fuel). Due to the increasing shortage of global petroleum resources and the long-term high-price operation of crude oil, the development of the light olefin industry relying only on a tubular cracking furnace technology that uses petroleum light hydrocarbon as raw material will encounter more and more difficulties in raw material. The production technology and the raw material of the light olefins must be diversified. A technology for preparing alkene using syngas can widen the source of the raw material, and will provide an alternative solution for a steam cracking technology based on high-cost raw material such as naphtha by production of syngas using crude oil, natural gas, coal and renewable material as raw material. One-step direct preparation of the light olefins using the syngas is a process of directly preparing the light olefins with the number of carbon atoms less than or equal to 4 through Fischer-Tropsch synthesis reaction of carbon monoxide and hydrogen under the action of the catalyst. This process simplifies the process flow and greatly reduces the investment unlike an indirect method that further prepares the alkene from the syngas and the methanol or dimethyl ether.

Direct preparation of the light olefins using the syngas through Fischer-Tropsch synthesis has become one of research hotspots in development of catalyst for Fischer-Tropsch synthesis. In patent CN1083415A disclosed by Dalian Institute of Chemical Physics, Chinese Academy of Sciences, high activity (CO conversion rate: 90%) and selectivity (light olefins selectivity: 66%) can be obtained under reaction pressure of 1.0 to 5.0 MPa and reaction temperature of 300 to 400° C. in preparation of the light olefins from the syngas under the auxiliary of alkali K or Cs ion by using an iron-manganese catalyst system carried by IIA alkali metal oxide such as MgO or silica rich zeolite (or phosphorous-aluminum zeolite). In patent ZL03109585.2 declared by Beijing University of Chemical Technology, Fe/activated carbon catalyst with manganese, copper, zinc, silicon and potassium as auxiliaries is prepared by a vacuum impregnation method for the reaction of preparation of the light olefins from the syngas. Under the condition of no feedstock gas circulation, the CO conversion rate is 96%, and the selectivity of the light olefins in hydrocarbons is 68%. In 2012, professor de Jong's team at Utrecht university in Netherlands made good progress by using Fe catalyst modified by Fe, Na, S and other auxiliaries supported by SiC, carbon nanofiber and other inert carriers, obtained 61% of selectivity of light olefins. However, the selectivity is reduced when the conversion rate is increased. In 2016, researcher Sun Yuhan and researcher Zhong Liangshu in Shanghai Advanced Research Institute reported a preferred exposure [101] and [020] manganese-assisted cobalt carbide based catalyst, and realized 60.8% of selectivity of light olefins and 5% of selectivity of methane at a CO conversion rate of 31.8%. In the above report, the catalyst uses an iron or cobalt based catalyst as an active component. The reaction follows the chain growth reaction mechanism of metal surfaces. The selectivity of the product light olefins is low.

Recently, a composite bifunctional catalyst of $ZnCr_2O_4$ oxide and hierarchical pore SAPO-34 zeolite has been reported by academician Bao Xinhe and professor Pan Xiulian in Dalian Institute of Chemical Physics, Chinese Academy of Sciences (Jiao et al., Science 351 (2016) 1065-1068), which has realized 80% of selectivity of the light olefins when the conversion rate of CO is 17%, wherein the selectivity of the light olefins is 14 and the alkene/alkane ratio is 5.7. When the conversion rate is increased to 35%, the alkene selectivity is 69%, alkane selectivity is 20%, and the alkene/alkane ratio is decreased to 3.5. How to achieve high conversion rate while stabilizing the alkene/alkane ratio is still a major difficulty in the field.

SUMMARY OF INVENTION

In view of the above problems, the present invention provides a catalyst and a method for preparing light olefins using direct conversion of syngas. The technical solution of the present invention is as follows:

A catalyst, characterized in that the catalyst is a composite catalyst A+B; the catalyst component A and the catalyst component B are compounded by mechanical mixing method; the active ingredient of the catalyst component A is an active metal oxide; catalyst B is one or more of zeolite of CHA and AEI structures with a carrier of one or more of $Al_2O_3$, $SiO_2$, $TiO_2$, $ZrO_2$, $CeO_2$, MgO and $Ga_2O_3$ having hierarchical pores; the loading of the zeolite in B is 4%-45% wt; and the active metal oxide is one or more than one of MnO, $MnCr_2O_4$, $MnAl_2O_4$, $MnZrO_4$, ZnO, $ZnCr_2O_4$, $ZnAl_2O_4$, $CoAl_2O_4$ and $FeAl_2O_4$.

The catalyst characterized in that one or more of hierarchical pores $Al_2O_3$, $SiO_2$, $TiO_2$, $ZrO_2$, $CeO_2$, MgO and $Ga_2O_3$ in the catalyst component B is used as the carrier; specific surface area is 30-250 m²/g; pore volume is 0.25-0.80 ml/g; through calculation according to the specific surface area, mesoporous specific surface area occupies 30-75% and macroporous specific surface area occupies 25-70%; and the zeolite is used as an active component and dispersed around the carrier by in situ growth or physical mixing mode.

The catalyst characterized in that component A is preferably one or more than one of MnO, $MnCr_2O_4$, $MnAl_2O_4$, $MnZrO_4$, $ZnAl_2O_4$, $CoAl_2O_4$ and $FeAl_2O_4$.

The catalyst characterized in that a spacing between geometric centers of the active metal oxide of the catalyst component A and the particle of the component B is 50 nm-20 mm, preferably 300 nm-5 mm and more preferably 1 μm-2.5 mm.

The catalyst characterized in that a weight ratio between the active ingredient in the catalyst component A and the catalyst component B is within the range of 0.1-20, and preferably 0.3-5.

The catalyst characterized in that the active metal oxide is composed of crystals with a size of 5-30 nm, and a large amount of oxygen vacancies exist within a distance range of 0.3 nm from the surfaces of the crystals to the internal direction of the crystals, wherein the molar weight of oxygen atoms occupies a value less than 80% of the oxygen molar content in theoretical stoichiometric ratio, preferably, 80%-10%, more preferably 60%-10% and most preferably 50%-10%; the surface oxygen vacancies are defined as: 100%-percent of the molar weight of oxygen atoms in theoretical stoichiometric ratio of oxygen molar weight; and corresponding oxygen vacancy concentration is preferably 20-90%, more preferably 40-90% and most preferably 50-90%.

The catalyst characterized in that a dispersing agent is also added to the catalyst A; the dispersing agent is one or more than one of $Al_2O_3$, $SiO_2$, $Cr_2O_3$, $ZrO_2$ and $TiO_2$; the active metal oxide is dispersed in the dispersing agent; and the content of the dispersing agent in the catalyst A is 0.05-90 wt %, and the balance is the active metal oxide.

A method for preparing light olefins using direct conversion of syngas, characterized in that syngas is used as reaction raw material; a conversion reaction is conducted on a fixed bed or a moving bed; and the adopted catalyst is the catalyst of any one of claims 1-7; the pressure of the syngas is 0.5-10 MPa; reaction temperature is 300-600° C.; space velocity is 300-10000 $h^{-1}$; and the ratio of syngas $H_2/CO$ for reaction is 0.2-3.5.

The dual-function composite catalyst is used for preparing light olefins using one-step direct conversion of syngas, wherein the sum of the selectivity of ethylene and propylene reaches 40-60%; the sum of the selectivity of the light olefins comprising ethylene, propylene and butylene can reach 50-90%, while the selectivity of a methane byproduct is less than 15%.

The present invention has the following advantages:

1. Different from the traditional technology for preparing the light olefins through methanol (MTO for short), this technology realizes preparation of the light olefins through one-step direct conversion of syngas.

2. Because of the hierarchical pore carrier dispersed zeolite, it is beneficial to the mass transfer of the intermediate and the product, thereby greatly reducing the influence of side reactions such as hydrogenation and maintaining high selectivity of the light olefins while increasing the conversion rate.

3. The composite catalyst in the patent is simple in preparation process and mild in conditions. The reaction process has an extremely high product yield and selectivity, with the selectivity for $C_2$-$C_4$ light olefins reaching 50-90% and especially can still maintain high alkene/alkane ratio after increasing the conversion rate. Meanwhile, the selectivity of the methane byproduct is low (<15%), and the catalyst has long service life which is longer than 700 hours. The present invention has excellent application prospect.

DETAILED DESCRIPTION

The present invention is further illustrated below by embodiments, but the scope of claims of the present invention is not limited by the embodiments. Meanwhile, the embodiments only give some conditions for achieving the purpose, but it doesn't mean that the conditions must be satisfied to achieve the purpose.

Embodiment 1

I. Preparation of Catalyst A (I) Synthesizing ZnO Material with Polar Surface Through an Etching Method Comprises:

(1) respectively weighing 4 parts of 0.446 g (1.5 mmol) of $Zn(NO_3)_2.6H_2O$ into four containers; respectively weighing 0.300 g (7.5 mmol), 0.480 g (12 mmol), 0.720 g (18 mmol) and 1.200 g (30 mmol) of NaOH and successively adding to the above four container; weighing 30 ml of deionized water and adding to the four containers; stirring for a time greater than 0.5 h to uniformly mix a solution; increasing the temperature to 160° C. with the reaction time of 20 h; decomposing precipitate into zinc oxide; naturally cooling to room temperature; centrifugally separating reaction liquid to collect the centrifugally separated precipitate; and washing with deionized water twice to obtain ZnO oxide;

taking a product with 0.480 g (12 mmol) of NaOH for the following processing:

(2) ultrasonically mixing an etching agent, such as oleic acid, hexamethylenetetramine, ethylenediamine, ammonia and hydrazine hydrate, with ZnO oxide uniformly under normal temperature; immersing the ZnO oxide in the solution of the etching agent; and generating a complexing or direct reduction reaction by the etching agent and the zinc oxide;

heating the above suspended matter; then taking out the suspended matter for washing and filtering the suspended matter to obtain active nano ZnO material having a large amount of surface oxygen holes.

In Table 1: the mass ratio of the catalyst to the etching agent is 1:3. The mass ratio of the oleic acid to the hexamethylenetetramine is 1:1, without solvent. The mass ratio of the oleic acid (5 wt %) to the hydrazine hydrate is 95:5, without solvent. Specific treatment conditions include the etching agent, temperature, treatment time and atmosphere types as shown in Table 1 below.

(3) Drying or Drying and Reducing:

after centrifuging or filtering the above obtained products and washing the products with deionized water, drying or drying and restoring the products in an atmosphere which is inert gas or a gas mixture of inert gas and a reducing atmosphere, wherein the inert gas is one or more than one of $N_2$, He and Ar, the reducing atmosphere is one or more than one of $H_2$ and CO; a volume ratio of the inert gas to the reducing gas in the dried and restored gas mixture is 100/10-0/100, the temperature of drying and restoring is 350° C., and time is 4 h. ZnO material with abundant oxygen vacancies on the surface is obtained. Specific samples and preparation conditions thereof are shown in Table 1 below. The surface oxygen vacancies are defined as: (1-percent of the molar weight of oxygen atoms in theoretical stoichiometric ratio of oxygen molar content).

TABLE 1

Preparation of ZnO Material and Parameter Performance

| Sample Number | Etching Agent | Temperature/° C. and carrier gas (V/V) | Ti (Minute) | Drying or Drying and Reducing Temperature/° C. and Atmosphere | Surface Oxygen Vacancy |
|---|---|---|---|---|---|
| ZnO 1 | oleic acid-hexamethylene tetramine | 100, $N_2$ | 30 | 30, $N_2$ | 21% |

TABLE 1-continued

Preparation of ZnO Material and Parameter Performance

| Sample Number | Etching Agent | Temperature/° C. and carrier gas (V/V) | Ti (Minute) | Drying or Drying and Reducing Temperature/° C. and Atmosphere | Surface Oxygen Vacancy |
|---|---|---|---|---|---|
| ZnO 2 | oleic acid | 100, 5% $H_2/N_2$ | 30 | 300, 5% $H_2/N_2$ | 45% |
| ZnO 3 | oleic acid | 120, 5% CO/Ar | 60 | 350, 5% CO/Ar | 67% |
| ZnO 4 | oleic acid-5 wt % hydrazine hydrate | 140, 5% $H_2$/Ar | 60 | 310, 5% $H_2$/Ar | 73% |
| ZnO 5 | ethylenediamine | 100, 5% $NH_3$/Ar | 30 | 250, 5% $NH_3$/Ar | 30% |
| ZnO 6 | ethylenediamine | 140, 5% NO/Ar | 90 | 150, 5% NO/Ar | 52% |
| ZnO 7 | 20 wt % ammonium hydroxide | 100, Ar | 30 | 120, 5% CO/Ar | 22% |
| ZnO 8 | 20 wt % ammonium hydroxide | 140, 5% $NH_3$/5% NO/Ar | 90 | 400, He | 29% |

The surface oxygen vacancies are the percent of the molar weight of oxygen atoms in theoretical stoichiometric ratio of oxygen molar content within a distance range of depth 0.3 nm from the surfaces of the crystals to the internal direction of the crystals.

As a reference example, the surface which is not etched in step (2) has no oxygen vacancy ZnO 9, and metal Zn 10 that completely reduces Zn.

(II) Synthesizing MnO material with polar surface through an etching method: the preparation process is the same as described in (I) (1) for the product with 0.480 g (12 mmol) of NaOH and (3). The difference is that, the precursor of Zn is changed for the corresponding precursor of Mn, which may be one of manganous nitrate, manganese chloride and manganese acetate, and is manganous nitrate herein.

The etching process is the same as the preparation processes of products ZnO 3, ZnO 5 and ZnO 8 in step (2) in above (I). The catalyst having a great number of surface oxygen vacancies is synthesized. The surface oxygen vacancies are 67%, 29% and 27%.

Corresponding products are defined as MnO 1-3.

(III) Synthesizing $CeO_2$ material with polar surface through an etching method: the preparation process is the same as that of the above (I)(1) for the product with 0.480 g (12 mmol) of NaOH and (3). The difference is that, the precursor of Zn is changed for the corresponding precursor of Ce, which may be one of cerium nitrate, cerium chloride and cerous acetate and is cerium nitrate herein.

The etching process is the same as the preparation processes of products ZnO 3, ZnO 5 and ZnO 8 in step (2) in above (I). The catalyst having a great number of surface oxygen vacancies is synthesized. The surface oxygen vacancies are 56%, 33% and 21%.

Corresponding products are defined as CeO 1-3.

(IV) Synthesizing nano $ZnCr_2O_4$, $ZnAl_2O_4$, $MnCr_2O_4$, $MnAl_2O_4$ and $MnZrO_4$ spinel with high specific surface area and high surface energy comprises:

adopting zinc nitrate, aluminum nitrate, chromic nitrate, manganous nitrate and zirconium nitrate as precursors, and mixing with urea at room temperature in water; aging the above mixed liquid; then taking out the mixed liquid for washing, filtering and drying the mixed liquid; and roasting the obtained solid under an air atmosphere to obtain spinel oxide which grows along the (110) crystal plane direction. The sample is also treated by the etching method to synthesize the catalyst with a great number of surface oxygen vacancies. The etching process and aftertreatment process are the same as step (2) and step (3) in above (I). The sample has large specific surface area and many surface defects, and can be applied to catalyzing the conversion of syngas.

Specific samples and preparation conditions thereof are shown in Table 2 below. Similarly, the surface oxygen vacancies are defined as: (1-percent of the molar weight of oxygen atoms in theoretical stoichiometric ratio of oxygen molar content).

TABLE 2

Preparation of Spinel Material and Performance Parameters

| Sample Number | Stoichiometric Ratio of Metal Elements in Spinel and Final Molar Concentration of Metal in Water (mmol/L) | Aging Temperature ° C. and Time h | Roasting Temperature ° C. and Time h | Etching Agent, Temperature/° C., Atmosphere and Time/min | Surface Oxygen Vacancy |
|---|---|---|---|---|---|
| spinel 1 | ZnCr = 1:2, Zn is 50 mM | 120, 24 | 600, 48 | oleic acid, 120, 5% $H_2$/Ar, 60 | 41% |
| spinel 2 | ZnAl = 1:2, Zn is 50 mM | 130, 20 | 700, 24 | oleic acid, 120, 5% $H_2$/Ar, 60 | 72% |
| spinel 3 | MnCr = 1:2, Mn is 50 mM | 140, 18 | 750, 16 | oleic acid, 120, 5% $H_2$/Ar, 60 | 83% |
| spinel 4 | MnAl = 1:2, Mn is 50 mM | 145, 16 | 800, 10 | oleic acid, 120, 5% $H_2$/Ar, 60 | 20% |
| spinel 5 | MnZr = 1:2, Mn is 50 mM | 150, 12 | 900, 3 | oleic acid, 120, 5% $H_2$/Ar, 60 | 24% |

(V) Synthesizing nano $FeAl_2O_4$, $CoAl_2O_4$ and spinel with high specific surface area and high surface energy: the preparation process is the same as (2) of the above (IV). The difference is that, the precursor of Zn is changed for the corresponding precursor of Fe or Co, which is one of ferric nitrate, ferric chloride and ferric citrate or one of cobalt nitrate, cobalt chloride and cobalt acetate and is ferric nitrate and cobalt nitrate herein.

The etching process is the same as the preparation processes of products ZnO 3 and ZnO 5 in step (2) in above (I). The catalyst having a great number of surface oxygen vacancies is synthesized. The surface oxygen vacancies are 77% and 51%.

Corresponding products are defined as spinel 6 and spinel 7.

(VI) $Cr_2O_3$, $Al_2O_3$ or $ZrO_2$ Dispersed Active Metal Oxide $Cr_2O_3$, $Al_2O_3$ or $ZrO_2$ dispersed active metal oxide is prepared through a precipitate deposition method by taking $Cr_2O_3$, $Al_2O_3$ or $ZrO_2$ as carriers. Taking preparation of oxide by dispersed ZnO as an example, commercial $Cr_2O_3$, $Al_2O_3$ or $ZrO_2$ carrier is dispersed in a base solution in advance, and then mixed and precipitated at room temperature with a sodium hydroxide precipitant by taking zinc nitrate as raw material. The molar concentration of $Zn^{2+}$ is 0.067M; and the ratio of molar fractions of $Zn^{2+}$ and the precipitant is 1:8; and then aging is conducted at 160° C. for 24 hours to obtain carrier $Cr_2O_3$, $Al_2O_3$ or $ZrO_2$ dispersed ZnO oxide (the contents of the dispersing agents in catalyst A are 0.1 wt %, 10 wt % and 90 wt %).

The etching process is the same as the preparation processes of products ZnO 3, ZnO 5 and ZnO 8 in step (2) in above (I). The catalyst having a great number of surface oxygen vacancies is synthesized. The surface oxygen vacancies are 65%, 30% and 25%. The aftertreatment process is the same as step (3) in above (I).

Corresponding products from top to bottom are defined as dispersed oxides 1-3.

The same method is used to obtain carrier $Cr_2O_3$, $Al_2O_3$ or $ZrO_2$ dispersed MnO oxide (the contents of the dispersing agents in catalyst A are 5 wt %, 30 wt % and 60 wt %). The surface oxygen vacancies are 62%, 27% and 28%. Corresponding products from top to bottom are defined as dispersed oxides 4-6.

II. Preparation of Catalyst B (Zeolite of CHA and AEI Topologies):

The CHA and/or AEI topology has eight-membered ring orifices and a three-dimensional porous channel and comprises cha cage.

1) The specific preparation process is as follows:

The raw materials of 30% (mass concentration) of silica sol, AlOOH, phosphoric acid, TEA (R) and deionized water are weighed according to oxide $SiO_2:Al_2O_3:H_3PO_4:R:H_2O=1.6:16:32:55:150$ (mass ratio); after mixing at room temperature, 0.5 time of molar weight of auxiliary HF is added to a template agent; carrier oxide powder is added; the mixture is stirred and aged at 30° C. and then transferred into a hydrothermal reactor after 2 h, and crystallized at 200° C. for 24 h. The water bath is quenched to room temperature. Centrifugal washing is conducted repeatedly so that the pH of the supernatant is 7 at the end of washing. After the precipitate is dried at 110° C. for 17 h, the precipitate is calcined in air at 600° C. for 3 h to obtain the supported silicon-phosphorus-aluminum inorganic solid acid.

The skeleton element composition of the zeolite of CHA and AEI topologies may be one or more than two of Si—O, Si—Al—O, Si—Al—P—O, Al—P—O, Ga—P—O, Ga—Si—Al—O, Zn—Al—P—O, Mg—Al—P—O and Co—Al—P—O.

O element of part of the skeleton is connected with H, and corresponding products are successively defined as parts 1-7.

TABLE 3

Preparation of Zeolite of CHA or AEI Topology and Performance Parameters

| Sample Number | Si Source | Aluminum Source | P Source | Template Agent | Auxiliary | Mass Ratio | Hydro-thermal | Time (Day) | Carrier | Molecular |
|---|---|---|---|---|---|---|---|---|---|---|
| part 1 | TEOS | sodium metaaluminate | phosphoric acid | TEA | | $SiO_2:Al_2O_3:H_3PO_4:R:H_2O = 1.6:16:32:55:150$ | 180 | 1 | $Al_2O_3$ | 4 |
| part 2 | silica sol | $Al(OH)_3$ | phosphoric acid | Mor | HCl | $SiO_2:Al_2O_3:H_3PO_4:R:H_2O = 2.4:19:30:15:150$ | 150 | 4 | $SiO_2$ | 15 |
| part 3 | TEOS | AlOOH | phosphoric acid | TEAOH | HF | $SiO_2:Al_2O_3:H_3PO_4:R:H_2O = 0.7:15:32:55:150$ | 160 | 4 | $TiO_2$ | 28 |
| part 4 | silica sol | aluminum isopropoxide | phosphoric acid | DIPEA | | $SiO_2:Al_2O_3:H_3PO_4:R:H_2O = 1.1:17:32:55:150$ | 170 | 2.5 | $ZrO_2$ | 34 |
| part 5 | | aluminum sulfate | phosphoric acid | TEAOH | HF | $Al_2O_3:H_3PO_4:R:H_2O = 16:32:55:150$ | 190 | 1 | $CeO_2$ | 24 |
| part 6 | silica sol | aluminum nitrate | phosphoric acid | DIPEA | | $SiO_2:Al_2O_3:H_3PO_4:R:H_2O = 0.5:17:32:55:150$ | 200 | 1 | MgO | 8 |
| part 7 | TEOS | aluminum sulfate | phosphoric acid | TEA | HF | $SiO_2:Al_2O_3:H_3PO_4:R:H_2O = 0.3:18:32:55:150$ | 170 | 0.7 | $Ga_2O_3$ | 20 |
| part 8 | | aluminum nitrate | phosphoric acid | TEA | HCl | $Al_2O_3:H_3PO_4:R:H_2O = 11:32:55:150$ | 160 | 3.5 | $Al_2O_3$ | 31 |

(2) Zeolite composed of other elements

| Sample Number | Precursor 1 | Precursor 2 | Precursor 3 | Template Agent | Auiliary | Mass Ratio | Hydro-thermal Temperature (° C.) | Time (Day) | Carrier | Molecular Sieve Loading wt % |
|---|---|---|---|---|---|---|---|---|---|---|
| part 9 | TEOS | | | TEA | HF | $SiO_2:R:H_2O = 1.6:55:150$ | 180 | 1 | $SiO_2$ | 45 |
| part 10 | silica sol | $Al(OH)_3$ | | Mor | HF | $SiO_2:Al_2O_3:R:H_2O = 2.4:19:15:150$ | 150 | 4 | $Al_2O_3$ | 10 |

TABLE 3-continued

Preparation of Zeolite of CHA or AEI Topology and Performance Parameters

| part 11 | | gallium nitrate | phosphoric acid | TEAOH | HF | Ga2O3:H$_3$PO$_4$:R:H$_2$O = 15:32:55:150 | 160 | 4 | TiO$_2$ | 22 |
| part 12 | silica sol | gallium nitrate | phosphoric acid | TEA | HF | SiO$_2$:Ga$_2$O$_3$:H$_3$PO$_4$:R:H$_2$O = 1.1:17:32:55:150 | 170 | 2.5 | ZrO$_2$ | 6 |
| Part 13 | zinc nitrate | aluminum sulfate | phosphoric acid | TEAOH | HF | ZnO:Al$_2$O$_3$:H$_3$PO$_4$:R:H$_2$O = 0.5:16:32:55:150 | 190 | 1 | CeO$_2$ | 25 |
| part 14 | magnesium nitrate | aluminum nitrate | phosphoric acid | TEA | | MgO:Al$_2$O$_3$:H$_3$PO$_4$:R:H$_2$O = 0.5:17:32:55:150 | 200 | 1 | MgO | 8 |
| part 15 | gallium nitrate | aluminum sulfate | phosphoric acid | TEA | HF | Ga2O3:Al$_2$O$_3$:H$_3$PO$_4$:R:H$_2$O = 0.4:18:32:55:150 | 170 | 0.7 | Ga$_2$O$_3$ | 11 |

The reference example is part 16; other conditions are the same as those of part 1; and the zeolite loading is changed to 1%.

The reference example is part 17; other conditions are the same as those of part 1; and the zeolite loading is changed to 70%.

III. Catalyst Preparation

The catalyst A and the catalyst B in the required ratio are added to the container to achieve the purposes of separation, crushing, uniform mixing and the like through one or more than two of extrusion force, impact force, shear force and friction force generated by high-speed motion of the material and/or the container, so as to realize conversion of mechanical energy, thermal energy and chemical energy by regulating the temperature and the atmosphere of carrier gas, thereby further enhancing the interaction between different components.

In the mechanical mixing process, the mixing temperature can be set as 20-100° C., and the mechanical mixing process can be conducted in an atmosphere or directly in the air. The atmosphere is one or more than one of: a) nitrogen and/or inert gas; b) mixed gas of hydrogen, nitrogen and/or inert gas, with the volume ratio of hydrogen in the mixed gas being 5-50%; c) mixed gas of carbon monoxide, nitrogen and/or inert gas, with the volume ratio of carbon monoxide in the mixed gas being 5-20%; and d) mixed gas of oxygen, nitrogen and/or inert gas, with the volume ratio of oxygen in the mixed gas being 5-20%. The inert gas is one or more than one of helium, argon and neon.

Mechanical stirring: mixing the catalyst A and the catalyst B with a stirring rod in a stirring tank; and regulating the mixing degree and the relative distance of the catalyst A and the catalyst B by controlling stirring time (5 min-120 min) and rate (30-300 r/min).

Ball milling: Rolling at high speed in a grinding tank by using abrasive and the catalysts; and producing strong impact and milling on the catalysts to achieve the effects of dispersing and mixing the catalyst A and the catalyst B. The ratio of the abrasive (which is stainless steel, agate and quartz; and the size range is 5 mm-15 mm) to the catalysts (the mass ratio scope is 20-100:1) is controlled to regulate the particle size and the relative distance of the catalysts.

Shaking table mixing: premixing the catalyst A and the catalyst B and placing the catalysts into the container; realizing the mixing of the catalyst A and the catalyst B by controlling the reciprocating oscillation or circumferential oscillation of a shaking table; and realizing uniform mixing and regulating the relative distance by regulating oscillation speed (range: 1-70 r/min) and time (range: 5 min-120 min).

Mechanical grinding: premixing the catalyst A and the catalyst B and placing the catalysts into the container; and under certain pressure (range: 5 kg-20 kg), making relative motion (speed range: 30-300 r/min) by the ground and mixed catalysts to achieve the effects of regulating the particle size and the relative distance of the catalysts and realizing uniform mixing.

Specific catalyst preparation and parameter features are shown in Table 6.

TABLE 6

Preparation of Catalysts and Parameter Features

| | | | | Compounding Mode and Condition | | | | |
| --- | --- | --- | --- | --- | --- | --- | --- | --- |
| Catalyst Number | Catalyst Component A | Catalyst Component B | Weight Ratio of A to B | Mechanical Agitation Rate (r/min) and Time (min) | Ball Milling Abrasive Material, Size Range and Catalyst Mass Ratio | Rocking Bed Oscillation Speed (r/min) and Time | Mechanical Polishing Pressure (kg) and Relative Movement Rate (r/min) | Geometrical Center Distance of A and B Particles |
| A | ZnO1 | part 1 | 0.33 | 170, 60 | | | | 50 μm |
| B | ZnO 2 | part 2 | 0.5 | 10, 50 | | | | 3 mm |
| C | ZnO3 | part 3 | 2 | | 5 mm stainless steel ball, 30:1 | | | 502 μm |
| D | ZnO4 | part 4 | 1 | | 6 mm stainless steel ball, 600:1 | | | 80 nm |
| E | ZnO 5 | part 5 | 1 | | | 5, 10 | | 1 mm |
| F | ZnO 6 | part 6 | 3 | | | 60, 100 | | 600 μm |
| G | ZnO7 | part 7 | 3 | | | | 50, 30 | 300 nm |
| H | ZnO8 | part 8 | 1 | 100, 300 | | | | 400 nm |
| I | spinel 1 | part 9 | 5 | | 6 mm agate ball, 110:1 | | | 40 μm |
| J | spinel 2 | part 10 | 1 | | | 70, 100 | | 500 μm |
| K | spinel 3 | part 11 | 3 | | | | 5, 20 | 2.5 mm |
| L | spinel 4 | part 12 | 0.33 | | | | 2, 30 | 4 mm |

TABLE 6-continued

Preparation of Catalysts and Parameter Features

| Catalyst Number | Catalyst Component A | Catalyst Component B | Weight Ratio of A to B | Mechanical Agitation Rate (r/min) and Time (min) | Ball Milling Abrasive Material, Size Range and Catalyst Mass Ratio | Rocking Bed Oscillation Speed (r/min) and Time | Mechanical Polishing Pressure (kg) and Relative Movement Rate (r/min) | Geometrical Center Distance of A and B Particles |
|---|---|---|---|---|---|---|---|---|
| M | spinel 5 | Part 13 | 1 | 10, 10 | | | | 2 mm |
| N | spinel 6 | part 14 | 3 | | 6 mm quartz, 10:1 | | | 1.5 mm |
| O | spinel 7 | part 15 | 0.33 | | 6 mm quartz, 10:1 | | | 1.5 mm |
| P | MnO 1 | part 1 | 1 | | | | 1, 10 | 2.5 mm |
| Q | MnO 2 | part 2 | 1 | 200, 250 | | | | 700 μm |
| R | MnO 3 | part 3 | 3 | | 5 mm stainless steel ball, 50:1 | | | 50 μm |
| S | CeO1 | part 4 | 1 | | | | 10, 100 | 100 μm |
| T | CeO2 | part 5 | 4 | | | 50, 600 | | 300 μm |
| U | CeO3 | part 6 | 3 | | | | 10, 100 | 100 μm |
| V | dispersed oxide 1 | part 7 | 20 | | 5 mm stainless steel ball, 10:1 | | | 3 mm |
| W | dispersed oxide 2 | part 8 | 0.5 | 5, 30 | | | | 3 mm |
| X | dispersed oxide 3 | part 9 | 1 | 100, 250 | | | | 500 μm |
| Y | dispersed oxide 4 | part 10 | 3 | | 5 mm stainless steel ball, 200:1 | | | 100 nm |
| Z | dispersed oxide 5 | part 11 | 1.5 | | 6 mm stainless steel ball, 60:1 | | | 8 μm |
| Z1 | dispersed oxide 6 | part 12 | 2.5 | | | 70, 100 | | 300 μm |
| Z2 | MnO 1 | Part 13 | 1.5 | | | 60, 100 | | 600 μm |
| Z3 | ZnO 1 | part 14 | 2 | | | | 50, 30 | 300 nm |
| Z4 | dispersed oxide 1 | part 15 | 10 | 100, 200 | | | | 400 μm |
| Z5 | spinel 1 | part 1 | 0.1 | | | | 20, 100 | 500 μm |
| Z6 | ZnO1 | part 1 | 1 | | | | 20, 300 | 100 μm |
| Z7 | MnO 1 | part 1 | 1.5 | 60, 10 | | | | 1 mm |
| Z8 | dispersed oxide 1 | part 1 | 4 | | 5 mm stainless steel ball, 50:1 | | | 15 μm |
| Z9 | spinel 1 | part 1 | 4.5 | | | 100, 120 | | 500 nm |
| Z10 | dispersed oxide 1 | part 1 | 2.5 | | | | 100, 200 | 400 nm |
| Z11 | spinel 1 | part 1 | 3 | | | | 20, 200 | 150 μm |
| Comparison 1 | ZnO 9 | part 1 | 3 | | | 20, 30 | | 1 mm |
| Comparison 2 | Zn 10 | part 1 | 2 | 60, 100 | | | | 1 mm |

Example of Catalytic Reactions

A fixed bed reaction is taken as an example, but the catalyst is also applicable to a fluidized bed reactor. The apparatus is equipped with gas mass flow meters and online product analysis chromatography (the tail gas of the reactor is directly connected with the metering valve of chromatography, and thus periodic and real-time sampling and analysis will be achieved).

2 g of the above catalyst in the present invention is placed in a fixed bed reactor. The air in the reactor is replaced with Ar; and then the temperature is raised to 300° C. in the $H_2$ atmosphere, and then the syngas ($H_2$/CO molar ratio=0.2-3.5) is switched. The pressure of the syngas is 0.5-10 MPa. The temperature is raised to reaction temperature of 300-600° C., and the air velocity of the reaction raw gas is regulated to 500-1000 ml/g/h. On-line chromatography is used to detect and analyze the product.

The reaction performance can be changed by changing the temperature, pressure, space velocity and $H_2$/CO molar ratio in the syngas. The sum of selectivity of the light olefins, the ethylene, the propylene and the butylene is 50-90%. Due to the low hydrogenation activity of the surface of the metal composite of the catalyst, a large amount of methane will not be avoided and the selectivity of the methane is low.

TABLE 7

Specific Application and Effect Data of Catalysts

| Embodiment | Catalyst | GHSV ($h^{-1}$) | Temperature (° C.) | $H_2$/CO Molar Ratio | Pressure (MPa) | CO Conversion | Light olefins | $CH_4$ Selectivity % | Alkene/Alkane Ratio |
|---|---|---|---|---|---|---|---|---|---|
| 1 | A | 8000 | 410 | 2 | 3.5 | 19.9 | 81.6 | 5.5 | 10.2 |
| 2 | B | 3000 | 400 | 5.5 | 0.9 | 33.6 | 80.3 | 5.6 | 10.0 |
| 3 | C | 8000 | 380 | 3 | 4.5 | 27.5 | 89.5 | 2.5 | 14.8 |
| 4 | D | 3000 | 370 | 6 | 10 | 29.4 | 68.8 | 13.5 | 5.3 |
| 5 | E | 10000 | 470 | 3.5 | 1.5 | 24.6 | 75.3 | 3.3 | 6.3 |
| 6 | F | 2000 | 400 | 4.5 | 7 | 51.3 | 81.9 | 2.6 | 8.2 |

TABLE 7-continued

Specific Application and Effect Data of Catalysts

| Embodiment | Catalyst | GHSV (h$^{-1}$) | Temperature (° C.) | H$_2$/CO Molar Ratio | Pressure (MPa) | CO Conversion | Light olefins | CH$_4$ Selectivity % | Alkene/ Alkane Ratio |
|---|---|---|---|---|---|---|---|---|---|
| 7 | G | 3000 | 380 | 6.5 | 2.5 | 34.7 | 73.9 | 11.7 | 10.6 |
| 8 | H | 500 | 370 | 8.5 | 5 | 33.5 | 69.9 | 10.8 | 7.0 |
| 9 | I | 2300 | 370 | 1 | 3.5 | 26.6 | 79.6 | 6.1 | 11.4 |
| 10 | J | 4000 | 410 | 2.5 | 5 | 35.6 | 88.7 | 2.7 | 17.7 |
| 11 | K | 1000 | 430 | 2.5 | 3 | 56.9. | 80.9 | 4.8 | 11.6 |
| 12 | L | 9500 | 520 | 1 | 4 | 14.6 | 85.9 | 8.1 | 14.3 |
| 13 | M | 600 | 480 | 0.5 | 9 | 15.3 | 65.7 | 12.5 | 4.4 |
| 14 | N | 9100 | 470 | 3 | 6 | 34.8 | 85.3 | 2.5 | 12.2 |
| 15 | O | 8200 | 450 | 1.5 | 5 | 33.9 | 84.7 | 2.9 | 14.1 |
| 16 | P | 8000 | 450 | 2.5 | 5 | 30.4 | 86.9 | 2.7 | 14.5 |
| 17 | Q | 600 | 350 | 3.5 | 5 | 25.6 | 73.8 | 3.5 | 6.2 |
| 18 | R | 2100 | 350 | 6 | 7 | 17.9 | 80.8 | 6.3 | 11.5 |
| 19 | S | 2500 | 400 | 4 | 6 | 55.7 | 77.7 | 6.1 | 11.1 |
| 20 | T | 4000 | 400 | 4 | 4 | 32.5 | 72.1 | 10.5 | 9.0 |
| 21 | U | 3500 | 400 | 4 | 3 | 24.9 | 74.0 | 9.7 | 6.2 |
| 22 | V | 8600 | 450 | 2.5 | 4 | 26.3 | 83.5 | 2.9 | 11.9 |
| 23 | W | 5500 | 410 | 0.3 | 3.5 | 15.8 | 84.6 | 3.7 | 14.1 |
| 24 | X | 3000 | 400 | 5.5 | 0.9 | 15.8 | 77.1 | 5.9 | 7.7 |
| 25 | Y | 2000 | 360 | 7 | 2.5 | 37.1 | 64.7 | 13.5 | 4.3 |
| 26 | Z | 800 | 370 | 5 | 10 | 40.3 | 71.9 | 11.6 | 5.1 |
| 27 | Z 1 | 10000 | 470 | 1.5 | 1.5 | 19.8 | 77.4 | 12.3 | 15.5 |
| 28 | Z 2 | 4000 | 400 | 3.5 | 7 | 48.6 | 87.5 | 3.7 | 17.5 |
| 29 | Z 3 | 3000 | 380 | 5.5 | 2.5 | 20.4 | 68.8 | 10.7 | 6.9 |
| 30 | Z 4 | 2000 | 400 | 4 | 3.5 | 15.3 | 51.6 | 11.7 | 2.9 |
| 31 | Z5 | 2500 | 400 | 4.5 | 10 | 17.7 | 53.7 | 3.9 | 2.8 |
| 32 | Z6 | 2000 | 350 | 3 | 4 | 15.8 | 78.3 | 2.8 | 6.5 |
| 33 | Z7 | 4500 | 400 | 2.5 | 3 | 46.6 | 85.7 | 3.1 | 9.5 |
| 34 | Z8 | 4000 | 400 | 3 | 4 | 53.9 | 86.0 | 3.5 | 12.3 |
| 35 | Z9 | 2000 | 350 | 2.5 | 3 | 27.9 | 70.3 | 8.8 | 6.4 |
| 36 | Z10 | 1500 | 350 | 3 | 4 | 31.4 | 68.9 | 9.6 | 5.7 |
| 37 | Z11 | 4200 | 400 | 2.5 | 4 | 34.4 | 77.2 | 3.5 | 6.4 |
| 38 | C | 4000 | 380 | 3 | 4.5 | 51.3 | 80.1 | 3.5 | 8.0 |
| 39 | J | 2000 | 410 | 2.5 | 5 | 52.9 | 81.4 | 2.4 | 8.1 |
| 40 | Reference example 1 | 3000 | 320 | 0.5 | 1 | 1.1 | 30.3 | 35.5 | 2.5 |
| 41 | Reference example 2 | 2000 | 350 | 1 | 2 | 18.7 | 37.5 | 45.9 | 2.5 |
| 42 | Reference example 3 | 4000 | 450 | 3 | 3 | 28.1 | 28.3 | 27.1 | 1.8 |
| 43 | Reference example 4 | 2000 | 350 | 2.5 | 3 | 0.3 | 27.3 | 61.7 | 1.6 |
| 44 | Reference example 5 | 2000 | 410 | 1.5 | 3 | 24.6 | 46.2 | 9.7 | 1.5 |
| 45 | Reference example 6 | 3000 | 400 | 2 | 3.5 | 31.2 | 19.5 | 10.8 | 0.9 |
| 46 | Reference example 7 | 8000 | 410 | 2 | 3.5 | 10.3 | 46.1 | 37.9 | 1.8 |
| 47 | Reference example 8 | 8000 | 410 | 2 | 3.5 | 52.1 | 43.7 | 28.1 | 1.7 |
| 48 | Reference example 9 | 8000 | 380 | 3 | 4.5 | 7.2 | 65.5 | 17.5 | 4.7 |
| 49 | Reference example 9 | 4000 | 380 | 3 | 4.5 | 13.6 | 48.1 | 15.5 | 1.6 |
| 50 | Reference Example 10 | 8000 | 380 | 3 | 4.5 | 38.4 | 49.5 | 2.5 | 1.3 |
| 51 | Reference Example 10 | 4000 | 380 | 3 | 4.5 | 52.5 | 37.1 | 3.5 | 0.7 |

In reference example 1, the catalyst component A is ZnO 9, and component B is part 1.

In reference example 2, the catalyst component A is Zn 10, and component B is part 1.

The component A in the catalyst adopted in reference example 3 is metal ZnCo+ part 1. The molar ratio of ZnCo is 1:1. The mass ratio of ZnCo to part 1 is 1:1. Other parameters and the mixing process are the same as those of catalyst C.

The catalyst adopted in reference example 4 is metal TiO$_2$+ part 1 without surface oxygen vacancy. Other parameters and the mixing process are the same as those of catalyst C.

The zeolite in the catalyst adopted in reference example 5 is a commodity SAPO-34 purchased from Nankai University Catalyst Factory without carrier dispersion.

The zeolite in the catalyst adopted in reference example 6 is a commodity ZSM-5 purchased from Nankai University Catalyst Factory, wherein the zeolite is of a full microporous structure, and the silica alumina ratio is 30, without carrier dispersion.

Reaction results of reference examples 5 and 6 show that, the topology and the carrier dispersion of CHA or AEI are crucial to the selective modulation of the products.

The distance between the metal oxide and the zeolite in the catalyst adopted in reference example 7 is 10 mm. Other parameters and the mixing process are the same as those of catalyst C.

The metal oxide in the catalyst adopted in reference example 8 is located in porous channels of the zeolite and is in close contact with the porous channels. Other parameters and the like are the same as those of catalyst C.

Results of reference examples 7 and 8 show that, the distance between component A and component B is also crucial to product selectivity.

In the reference technology of the document (Jiao et al., Science 351 (2016) 1065-1068), the SAPO-34 zeolite contained no carrier. When the conversion rate is 17, alkene selectivity is 80%, but the space velocity is reduced. When the conversion rate is increased to 35%, alkene selectivity is 69%, alkane selectivity is 20%, and alkene/alkane ratio is decreased to 3.5.

For the catalysts in the reference examples 9 and 10, other conditions are the same as those of C; and only the zeolites are respectively replaced with part 16 and part 17.

It can be seen from the reference example 9 that, the zeolite loading is too low, which results in slightly high selectivity of methane and slightly low selectivity of alkene.

It can be seen from the reference example 10 that, the zeolite loading is too high, which results in excessive hydrogenation and slightly low selectivity of alkene. Especially after the space velocity is reduced and the conversion rate is increased, compared with the catalyst C, the alkene/alkane ratio is obviously reduced.

It is observed that from the above table that, the structure of the zeolite including the topologies, acid strength and acid amount of CHA&AEI, and the matching of the distance between the metal oxide and the zeolite are crucial and directly affect the conversion rate of carbon monoxide and propylene and butylene selectivity.

The invention claimed is:

1. A catalyst comprising catalyst component A and catalyst component B,
wherein the catalyst component A and the catalyst component B are mechanically mixed, wherein the catalyst component A comprises a metal oxide and the catalyst component B comprises a zeolite supported on a carrier,
wherein the carrier is selected from porous $Al_2O_3$, $SiO_2$, $TiO_2$, $ZrO_2$, $CeO_2$, MgO, $Ga_2O_3$, and mixtures thereof, the zeolite is selected from a CHA zeolite, an AEI zeolite, or mixtures thereof, wherein a loading of the zeolite is 4%-45% wt of the component B; and the metal oxide is selected from MnO, $MnCr_2O_4$, $MnAl_2O_4$, $MnZrO_4$, $ZnCr_2O_4$, $ZnAl_2O_4$, $CoAl_2O_4$, $FeAl_2O_4$, and mixtures thereof.

2. The catalyst according to claim 1, wherein the carrier has a specific surface area of 30-250 $m^2/g$, a pore volume of 0.25-0.80 ml/g, a mesoporous specific surface area of 30-75% and a macroporous specific surface area of 25-70% of the specific surface area.

3. The catalyst according to claim 1, wherein component A is selected from $MnCr_2O_4$, $MnAl_2O_4$, $MnZrO_4$, $ZnAl_2O_4$, $CoAl_2O_4$, $FeAl_2O_4$, and mixtures thereof.

4. The catalyst according to claim 1, wherein a weight ratio between the metal oxide in the catalyst component A and the catalyst component B is within a range of 0.1-20.

5. The catalyst according to claim 1, wherein the metal oxide is in a form of crystals having a size of 5-30 nm, and oxygen vacancies residing within a depth of 0.3 nm from a surface of the crystal, wherein a weight of oxygen atoms in the metal oxide is less than 80% of a weight of a stoichiometric amount of oxygen atoms in the metal oxide.

6. The catalyst according to claim 1, wherein the catalyst component A further comprises a dispersing agent selected from $Al_2O_3$, $SiO_2$, $Cr_2O_3$, $ZrO_2$, $TiO_2$, and mixtures thereof, and a weight of the dispersing agent is 0.05-90 wt % of the weight of the catalyst component A.

7. A method for synthesis of light olefins directly from syngas, comprising contacting a syngas with the catalyst of claim 1 at a pressure of the syngas of 0.5-10 MPa, a reaction temperature of 300-600° C., a syngas space velocity of 300-10000 $h^{-1}$, and wherein a molar ratio of $H_2$ to CO in the syngas is 0.2-3.5.

8. The catalyst according to claim 4, wherein the weight ratio is within the range of 0.3-5.

9. The catalyst according to claim 5, wherein the weight of oxygen atoms in the metal oxide is 10%-80% of the weight of a stoichiometric amount of oxygen atoms in the metal oxide.

10. The catalyst according to claim 5, wherein a oxygen vacancy is 20-90%, wherein the oxygen vacancy is a percentage of a weight of oxygen atoms in the metal oxide in a weight of the stoichiometric amount of oxygen atoms in the metal oxide.

11. The catalyst according to claim 10, wherein the oxygen vacancy is 40-90%.

12. The catalyst according to claim 11, wherein the surface oxygen vacancy is 50-90%.

13. The catalyst according to claim 1, consisting of the catalyst component A and the catalyst component B.

14. The catalyst according to claim 1, wherein the mechanical mixing is stirring, ball milling, shaking table mixing, or grinding.

* * * * *